(12) United States Patent
Thomas

(10) Patent No.: US 7,121,475 B2
(45) Date of Patent: Oct. 17, 2006

(54) HUNTING DEVICE FOR CARRYING AND RETAINING ANIMAL SCENT

(75) Inventor: Gary W. Thomas, 606 Summit St., Marshalltown, IA (US) 50158

(73) Assignee: Gary W. Thomas, Marshalltown, IA (US)

( * ) Notice: Subject to any disclaimer, the term of this patent is extended or adjusted under 35 U.S.C. 154(b) by 102 days.

(21) Appl. No.: 10/939,730

(22) Filed: Sep. 13, 2004

(65) Prior Publication Data

US 2006/0054715 A1   Mar. 16, 2006

(51) Int. Cl.
*A61L 9/04* (2006.01)
*A01M 31/00* (2006.01)

(52) U.S. Cl. .......................... 239/53; 239/36; 239/51.5; 239/34; 43/1

(58) Field of Classification Search .................. 239/36, 239/44, 51.5, 53, 34, 47, 55–57, 152, 153, 239/326; 43/1; 119/654, 858, 860; 132/273, 132/246; 63/3, 5.1, 11, DIG. 2
See application file for complete search history.

(56) References Cited

U.S. PATENT DOCUMENTS

| | | | |
|---|---|---|---|
| 1,780,407 A | * | 11/1930 | Smith ........................... 239/36 |
| 2,626,833 A | | 1/1953 | Valentine |
| 3,896,995 A | * | 7/1975 | Lelicoff ........................ 239/36 |
| 4,047,505 A | | 9/1977 | McAndless |
| 4,356,969 A | | 11/1982 | Obermayer et al. |
| 4,722,477 A | | 2/1988 | Floyd |
| 4,735,010 A | | 4/1988 | Grinarml |
| 4,881,671 A | | 11/1989 | Horton et al. |
| 5,074,439 A | | 12/1991 | Wilcox |
| 5,109,803 A | * | 5/1992 | Dunham et al. ............ 119/654 |
| 5,327,667 A | | 7/1994 | Fore |
| 5,738,398 A | * | 4/1998 | Miano ......................... 294/1.1 |
| 5,823,432 A | * | 10/1998 | Hogan ........................ 239/36 |
| 5,857,217 A | * | 1/1999 | Hsueh ........................... 2/170 |
| 6,227,207 B1 | * | 5/2001 | Stachowski ................ 132/273 |
| 6,712,286 B1 | | 3/2004 | Baxter et al. |
| 2002/0117556 A1 | | 8/2002 | Putz |

* cited by examiner

*Primary Examiner*—David A. Scherbel
*Assistant Examiner*—Darren Gorman

(57) ABSTRACT

An improved device for carrying and retaining animal scent that has a specially designed sleeve having an absorbent pad for absorbing a liquid scent that attracts prey wherein the absorbent pad has a plurality of apertures to facilitate the aeration of the scent and additionally the sleeve has a slit such that a resilient self attaching band can be placed therein so that the sleeve may be attached to objects and yet the resilient band can be removed so that the cover can be properly washed.

5 Claims, 2 Drawing Sheets

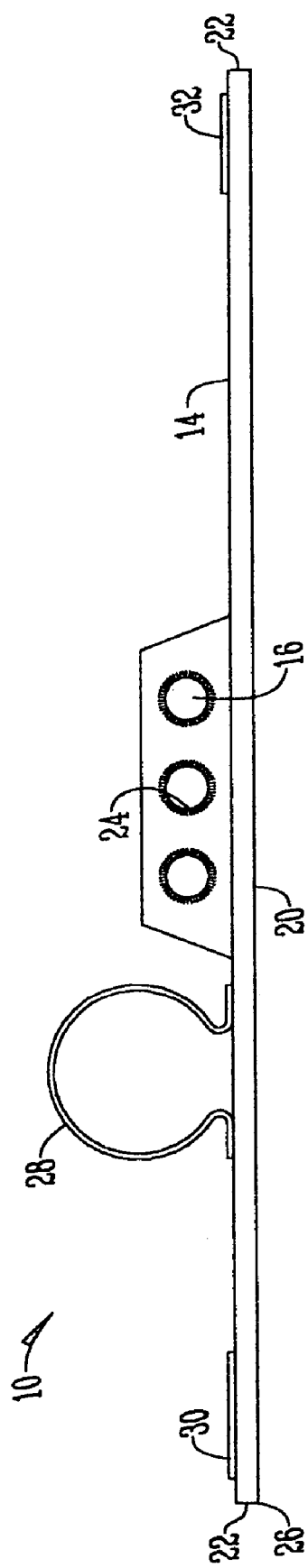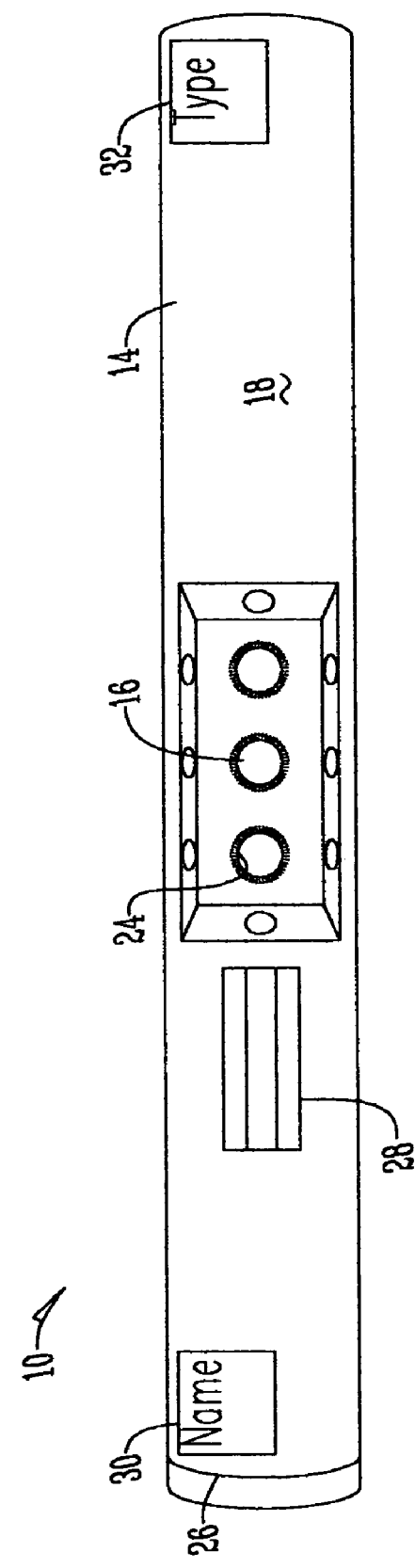

HUNTING DEVICE FOR CARRYING AND RETAINING ANIMAL SCENT

BACKGROUND OF THE INVENTION

This invention relates to a hunting device. More specifically, this invention relates to a hunting device for carrying and retaining animal scent that attracts prey.

Hunters of deer and other game animals frequently will rely on some type of animal lure to assist them in tracking and sighting game. Usually, the lure a hunter employs is a scented substance, the odor of which is an animal attractant. Other scented substances likewise are used to mask the natural odors associated with the hunter that would otherwise warn the animal of the hunter's presence thereby hindering the hunter's ability to attract the animal.

Many of the commercially available scented substances are provided in liquid form and applied directly to the clothes or boots of the hunter. The scent, however, ordinarily wears off relatively quickly because of the type of fabrics commonly used for hunting apparel. This tendency is exacerbated by rain and other weather conditions the hunter frequently encounters during an outdoor extrusion, as well as by the hunter brushing against trees limbs and shrubs as the hunter moves through a wooded area in pursuit of prey.

Various types of devices have attempted to solve the stated problems. For example, devices have been designed that involve an elongated flexible metal band that is able to attach itself by being struck against an object and wrapping itself around that object. In combination with this band a cover is placed over the top of the band that has an absorbent material that will absorb scented liquid so that the band may be placed around a tree or around a wrist and emit the scent. Though effective dispensing scent into the environment for a short period of time, problems with this device still remain. For example, there is a problem in the art in properly releasing the scent from the cover into the atmosphere such that a strong odor will occur thus attracting prey towards the band.

Another problem in the art is that the cover upon use, permanently has the liquid scent thereon. Consequently, many hunters are unwilling to keep the band and store it because the scent remains after the hunting is complete.

An additional problem is present in storing the devices when more than one device is used having different scents, confusion can occur over which device carries which scent. When hunting seasons are months apart this can at times be difficult.

Another problem in the art is that removal of current devices from limbs can be difficult. Currently one must pry the device off of an object and during extremely cold whether when the fingers of a hunter become numb removal becomes very difficult.

Consequently, there is a need in the art for an improved device for carrying and retaining animal scent that not only provides better aeration properties than previous scent dispensers but also is able to be washed or cleaned effectively so it may be reused several times. Additionally there is a need in the art to identify the type of scent a device is carrying and to provide for a means of easy removal of the device from an object.

Therefore, the principal object of the present invention is to provide an improved device for carrying and retaining animal scent that minimizes the restriction of aeration of the scent.

Yet another object of the present invention is to provide a device for carrying and retaining animal scent that may be easily washed to facilitate reuse.

Another object of the present invention is to provide an identification means on a scented hunting device to identify the type of scent contained by the device.

Yet another object of the present invention is to provide a means for easy removal of a scent device from an object.

These and other objects, features, or advantages of the present invention will become apparent from the specification and claims.

BRIEF SUMMARY OF THE INVENTION

The present invention is a device for carrying and retaining animal scent. The device consists of an elongated flexible member that is able to wrap around an object when it is struck against that object and is placed in a specially designed sleeve. The sleeve is specially designed to have a pad that absorbs a liquid scent of an animal thus emitting the scent into the air. The padded area is additionally designed to have a plurality of apertures that are aligned in order to facilitate the aeration process thus maximizing the scent provided in the air. Additionally, the sleeve is designed to have a slit such that the thin flexible elongated member can be placed within the sleeve or removed from the sleeve thus allowing the sleeve to be separated so the sleeve may be washed in a conventional manner.

BRIEF DESCRIPTION OF THE DRAWINGS

FIG. 1 is a side plan view of the present invention;

FIG. 2 is a plan top view of the present invention; and

DETAILED DESCRIPTION OF THE INVENTION

Figure 3:
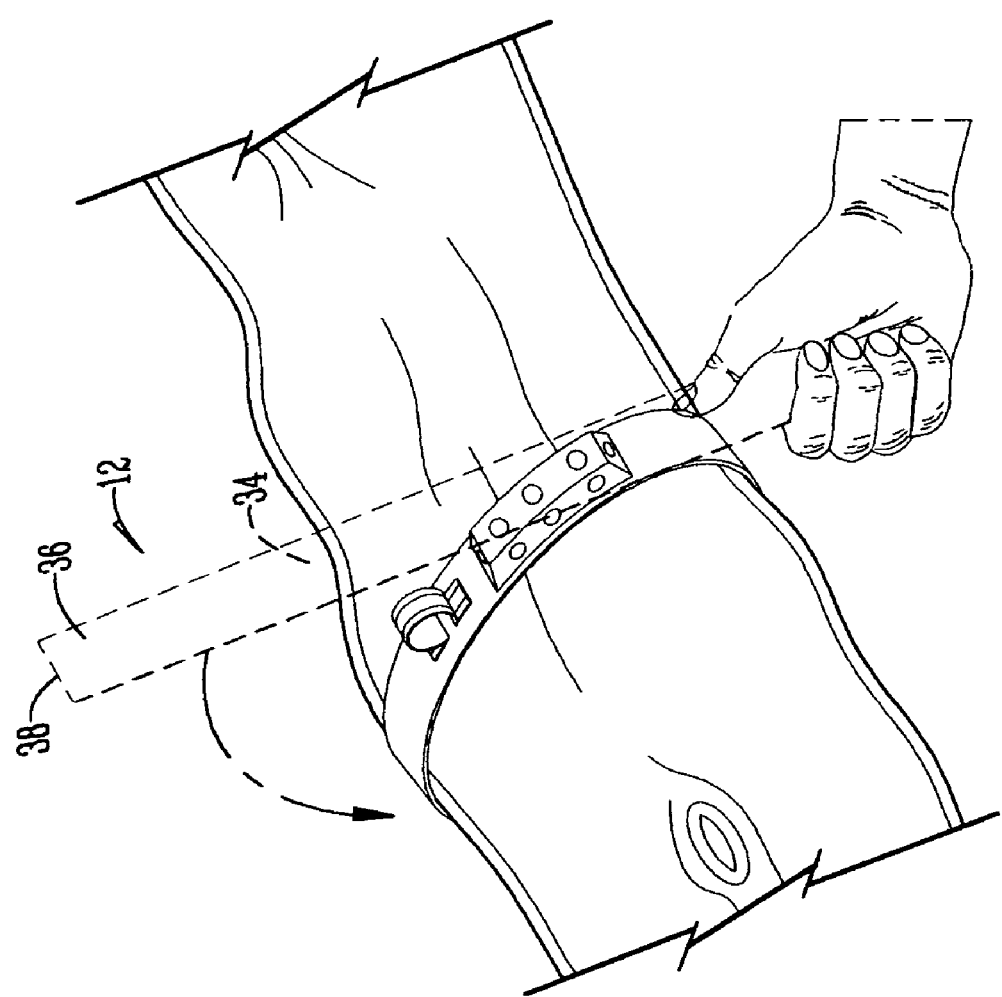
FIG. 3 is a perspective view of the present invention attaching itself to a limb.

FIG. 1 shows a device 10 for changing and retaining animal scent. The device 10 is comprised of two separate parts; an elongated resilient band 12 (FIG. 3) and a sleeve 14.

The sleeve 14 is designed to have an absorbent pad 16 that is able to absorb liquid animal scent. The sleeve 14 is also designed to have a pouch area for pad 16 having a top 18, sides 20, and first and ends 22. The top 18 and sides 20 have a plurality of scent apertures 24 thereon to facilitate the aeration of the scent from the absorbent pad 16 into the environment. Additionally, apertures can be placed on the ends 22 of the absorbent pad 16. Also, the end of the cover has a releasable slit 26 that allows the flexible member 12 to be inserted into the sleeve and removed. A fastening means such as Velcro® can be used to seal the slit. Consequently, after use of the sleeve 14, the flexible member 12 can be released and the sleeve can be placed in a conventional washer to eradicate the urine smell from the pad 16 so a hunter can store the device 10 and reuse it during the next hunt. Optionally, the slit 26 can be located on the back surface of the sleeve 14.

One skilled in the art will appreciate that the sleeve 14 is made of a material that will allow additional features to be included on the device. For example, a finger tab 28 may be fastened to the sleeve 14 so that when the weather is cold and a hunter's fingers are numb the device 10 can be quickly removed from an object. Additionally the tab 28 can be made from reflective tape, thus allowing hunters to find the device at night with a light source. Another feature that can be added to the sleeve 14 is the use of indicia tags, such as a name tag 30 to identify the hunter or a scent tag 32 to ensure the hunter is using the correct device. Additionally the sleeve 14 can be made of camouflaged material to hide the device 10 from the hunted animal.

As best seen in FIG. 3 the elongated flexible member 12 has a substantially elongated body 34 that has a substantially convex first surface 36, the direction of curvature of the convex surface 36 being substantially perpendicular to the direction of elongation of the substantially elongated body 34, and substantially concave second surface 38, the second surface 38 being opposite the first surface 36 and the direction of curvature of the concave surface, again, being substantially perpendicular to the direction of elongation of the substantially elongated body 34. Because of the substantially elongated body 34, it is intentionally formed with a bias toward a coiled alignment, the body 34 naturally possesses potential energy when stretched to its fully elongated shape. The convex first surface 36 and the concave second surface 38, however, impart a curvature along and, preferably, substantially centered around the longitudinal axis of the body 34. Thus formed, the elongated flexible member 12, despite its bias toward a coiled alignment, can be stretched into a substantially elongated alignment with the convex and concave surfaces of the elongated body 34 supplying resistance to the body's natural tendency to coil. That is, despite the body's potential energy when stretched longitudinally, the curvature supplied by shape of the convex surface 36 and the concave surface 38 allow the body 34 to remain in equilibrium.

When struck against a pre selected object, however, the body's tendency to coil is not impeded, as the force of the blow tends to flatten out the convex and concave surfaces 36 and 38. To attach the elongated flexible member 12, the user need only strike the member 12 against the pre selected object with enough force to overcome the obstacle posed by the curvature around the longitudinal axis formed as a result of the convexity of the first surface 18 and concavity of the second surface 38. As the respective surfaces flatten out, the released potential energy is made available to drive the body 34 into a more stable equilibrium; a coiled alignment. Thus, when struck against the pre selected object, the elongated flexible member 12 self fastens by coiling substantially around the object against which it has struck. Thus one skilled in the art will appreciate that because of the self fastening property the flexible member 12 may be attached to a hunters wrist or cap, or could be attached to tree limbs and hunting traps.

In operation, a hunter identifies the sleeve he wants use by reading the scent tag 32 and then takes the flexible member 12 and places it through the slit 26 of sleeve 14 to assemble the present device 10. A hunter will then place scented liquid on the absorbent pad 16 and attach the device to a limb by striking the device 10 against the object and allowing it to self fasten as described. The apertures 24 then allow the scent to aerate into the open air to provide a strong scent for prey to detect. Thus, the apertures 24 provide a means for providing a stronger scent. When the hunt is finished the hunter places his finger in the finger tab 28 and removes the device 10 from the object. Once home the flexible member 12 is removed through the slit 26 allowing for the sleeve 14 to be washed and therefore more easily stored and reused. Consequently, the device accomplishes all of its stated objectives.

It will be appreciated by those skilled in the art that other various modifications could be made to the device without the parting from the spirit in scope of this invention. All such modifications and changes fall within the scope of the claims and are intended to be covered thereby.

What is claimed is:

1. A hunting device for dispensing scent comprising:
   an elongated resilient band comprising a substantially elongated body having a substantially convex first surface, a substantially concave second surface, with a bias toward coiled alignment;
   a sleeve having a releasable slit for receiving the resilient band;
   an absorbent pad disposed within an interior of the sleeve; and
   the sleeve having at least one aperture adjacent the absorbent pad.

2. The hunting device of claim 1 wherein the releasable slit is in an end of the sleeve.

3. The hunting device of claim 2 wherein the slit is sealed by a fastening means.

4. The hunting device of claim 1 further comprising a finger tab attached to the sleeve.

5. The hunting device of claim 1 further comprising an indicia tag attached to the sleeve.

* * * * *